(12) United States Patent
Woo et al.

(10) Patent No.: US 7,166,305 B2
(45) Date of Patent: Jan. 23, 2007

(54) POLYVALENT METAL-SUBSTITUTED STARCH PRODUCTS

(75) Inventors: Kyungsoo Woo, Platte City, MO (US); Clodualdo Maningat, Platte City, MO (US); Sukh Bassi, Atchison, KS (US)

(73) Assignee: MGP Ingredients, Inc., Atchison, KS (US)

( * ) Notice: Subject to any disclaimer, the term of this patent is extended or adjusted under 35 U.S.C. 154(b) by 60 days.

(21) Appl. No.: 10/459,167

(22) Filed: Jun. 11, 2003

(65) Prior Publication Data

US 2004/0253201 A1 Dec. 16, 2004

(51) Int. Cl.
*A61K 47/00* (2006.01)
*A61K 9/14* (2006.01)
*A61K 9/16* (2006.01)

(52) U.S. Cl. ............... 424/488; 424/439; 424/484; 424/489; 424/494

(58) Field of Classification Search ............ 424/488
See application file for complete search history.

(56) References Cited

U.S. PATENT DOCUMENTS

| | | | |
|---|---|---|---|
| 2,461,139 A | | 5/1949 | Caldwell |
| 2,613,206 A | * | 11/1952 | Caldwell et al. ............ 252/384 |
| 2,661,349 A | | 12/1953 | Caldwell et al. |
| 3,746,558 A | * | 7/1973 | Berkhout et al. ........ 106/207.1 |
| 5,151,264 A | | 9/1992 | Samain et al. |
| 5,256,404 A | | 10/1993 | Martino et al. |
| 5,855,946 A | | 1/1999 | Seib et al. |
| 5,858,993 A | * | 1/1999 | Pickart ........................ 514/60 |
| 5,882,713 A | | 3/1999 | Eskins et al. |
| 6,299,907 B1 | * | 10/2001 | Seib et al. .................. 424/499 |
| 2002/0168408 A1 | | 11/2002 | Samain et al. |

FOREIGN PATENT DOCUMENTS

| | | |
|---|---|---|
| EP | 0 761 691 A2 | 12/1997 |
| EP | 0761691 | * 12/1997 |

OTHER PUBLICATIONS

Modified Starches: Properties and Uses; O.B. Wurzburg; pp. 132-147.
Starch: Chemistry and Technology; Roy Whistler, James Bemiller, and Eugene Paschall; pp. 341-343; 1984.
Studies of Starch Esterification: Reactions with Alkenylsuccinates in Aqueous Slurry Systems; Young-Seaon Jeon, Arvind Visawanathan, and Richard Gross, pp. 90-93; 1999.
Distribution of Octenyl Succinate Groups in Octenyl Succinic Anhydride Modified Waxy Maize Starch; Randal Shogren, Arvind Viswanathan, Frederick Felker, and Richard Gross; pp. 196-2004; 2000.
Protection of Unstable Vitamins, Enzymes and Natural Free Radical Scavengers By Novel Delivery Systems; L. Ding; Personal Care Ingredients Asia, vol. 1, Apr. 1999; pp. 114-125.

* cited by examiner

*Primary Examiner*—Michael P. Woodward
*Assistant Examiner*—David Vanik
(74) *Attorney, Agent, or Firm*—Hovey Williams LLP

(57) ABSTRACT

Improved starch-metal derivatives are provided which have excellent dry flow characteristics and ready dispersability in hot or cold water. The preferred derivatives comprise granules of starch which have been expanded or preswelled and cross-linked, followed by reaction with a polyvalent metal salt, especially salts of Ca, Mg, Zn Cu and Al.

11 Claims, 4 Drawing Sheets

POLYVALENT METAL-SUBSTITUTED STARCH PRODUCTS

BACKGROUND

1. Field of the Invention

The present invention is concerned with improved modified starch-polyvalent metal derivatives and methods of preparation thereof, wherein the starches are preferably preswelled or expanded and both chemically cross-linked and substituted with hydrophobic moieties prior to substitution with polyvalent metals. The resultant starch derivatives are free-flowing in a dry state and exhibit extremely rapid and easy hydration in hot or cold water. The preferred starches are prepared by initially preswelling and cross-linking native starch, followed by subjecting the preswelled/cross-linked starch to a substitution reaction using a hydrophobic agent such as an acid or acid anhydride; thereafter, the starch is reacted with a metal salt resulting in metal substitution through bridging of hydrophobic moieties.

2. Description of the Prior Art

The preparation of starches including hydrophobic substituent groups is well known. U.S. Pat. No. 2,661,349 describes the preparation of such products by a reaction of starch in an aqueous alkaline slurry and in the presence of a hydrophobic agent. The '349 patent also describes other preparative methods using an organic suspension or discussion.

The esterification of starch with hydrophobic substituents such as octenyl succinic anhydride is described by Trubiano (*Modified Starches: Properties and Uses*, p. 131–147 (1986)) and Rutenburg et al. (*Starch Chemistry and Technology*, 2nd ed. p. 341–343 (1984)). Such prior art substituted starch products tend to swell excessively and fuse together upon discussion in water and heating above the granule melting or gelatinization temperature of the starch. After cooking, these products do not retain granular structure but rather agglomerate to form paste-like systems.

U.S. Pat. No. 5,882,713 describes non-separable compositions of starch and water-immiscible materials by solu-ablization of starch granules in a stream of water and steam under high turbulence conditions. Such products are characterized as: being stable without phase separation on prolonged standing; forming soft gels upon heating; forming dried, non-oily solids upon drying; and easy hydration in water to form stable and homogeneous dispersions. In the process of the '713 patent, starch is fully solubilized and aligned at the interface of oil and water phases to form thick and gel-like films about oil or lipid droplets.

In 1987 Englyst and Cummings at the MRC Dunn Clinical Nutrition Center in Cambridge, UK, proposed a classification of starch based on its likely digestive properties in vivo. They also devised in vitro assay methods to mimic the various digestive properties of starch. Three classes of dietary starch were proposed:

(1) Rapidly Digestible Starch (RDS). RDS is likely to be rapidly digested in the human small intestine; examples include freshly cooked rice and potato, and some instant breakfast cereals.

(2) Slowly Digestible Starch (SDS). SDS is likely to be slowly yet completely digested in the small intestine; examples include raw cereal starch and cooked pasta.

(3) Resistant Starch (RS). RS is likely to resist digestion in the small intestine. RS is thus defined as the sum of starch and starch degradation products not likely to be absorbed in the small intestine of healthy individuals. RS can be subdivided into four categories depending on the cause of resistance (Englyst et al *Eur. J. Clin. Nutr.* 46(suppl 2):S33, 1992; Eerlingen et al *Cereal Chem.* 70:339, 1993).

$RS_1$. Physically inaccessible starch due to entrapment of granules within a protein matrix or within a plant cell wall, such as in partially milled grain or legumes after cooling.

$RS_2$. Raw starch granules, such as those from potato or green banana, that resist digestion by α-amylase, possibly because those granules lack micropores through their surface.

$RS_3$. Retrograded amylose formed by heat/moisture treatment of starch or starch foods, such as occurs in cooked/cooled potato and corn flake.

$RS_4$. Chemically modified starches, such as acetylated, hydroxypropylated, or cross-linked starches that resist digestion by alpha-amylase. Those modified starches would be detected by the in vitro assay of RS. However, some $RS_4$ may not be fermented in the colon.

$RS_1$, $RS_2$, $RS_3$ are physically modified forms of starch and become accessible to α-amylase digestion upon solubilization in sodium hydroxide or dimethyl sulfoxide. $RS_4$ that is chemically substituted remains resistant to α-amylase digestion even if dissolved. $RS_4$ produced by cross-linking would resist dissolution.

U.S. Pat. No. 6,299,907 describes improved resistant starches which are modified so as to be reversibly swellable. These starch products have a number of novel properties including the capability of undergoing multiple cycles of swelling and drying while substantially retaining the individuality of the starch granules and with the presence of very small amounts of starch solubles. These products also exhibit swelling powers enabling them to absorb water in excess of their own weights. However, when mixed with hot or cold water, these starch products eventually precipitate toward the bottom of the water phase, which may limit wide applicability of the products in water/oil emulsion systems.

U.S. Pat. No. 5,151,264 and Publication U.S. 2002/0168408 describe starch-based vectors used for the transport of biologically active molecules. These vectors include a cross-linked starch core with a first layer or ring of lipid material bonded to the core and a second layer or outer shell of amphiphilic compounds bonded to the lipid layer. However, these references do not describe the use of a preswelled or expanded starch core.

U.S. Pat. No. 5,858,993 describes starch-metal complexes useful for accelerating the healing of topical wounds or as a hair growth stimulant. The complexes described in the '993 patent are prepared by using native starch granules which are first pasted and then reacted with relatively high concentrations of copper(II) or tin(II) salts. There is no teaching in this patent regarding metal substitution of cross-linked starches or expanded or preswelled starches.

SUMMARY OF THE INVENTION

The present invention provides improved modified starch derivatives which are free-flowing in a dry state and very rapidly hydrate in hot or cold water. The starch derivatives of the invention may be directly prepared using native starch and selected polyvalent metal salts, particularly those of Groups 2–10 of the Periodic Table using the modern arabic numeral Group designations. More preferably however, the derivatives are prepared using starch granules which are initially preswelled or expanded and chemically cross-linked and thereafter substituted with a plurality of hydrophobic moieties normally on the surface of the starch granules. Preswelling and cross-linking of the starch granules can be carried out in a number of ways preferably by a preswelling/cross linking reaction as described in U.S. Pat. No. 6,299,907. However prepared, the cross-linked starch products are then reacted with a hydrophobic agent so as to cause hydrophobic moieties to chemically react with the granules. In the final step of preparation, the preswelled/modified starches are reacted with an appropriate metal salt selected from the group consisting of the polyvalent metals of Groups 2–13, inclusive, of the Periodic Table, and most especially salts of calcium, magnesium, zinc and aluminum.

Virtually any starch may be derivatized in accordance with the invention, although the relatively inexpensive starches as wheat and corn starches are preferred. Where cross-linked starches are employed, numerous cross-linking agents may be used, but for ease of preparation the common phosphate-based cross-linkers are preferred. The hydrophobic agents used in preparation of the preferred starches hereof are usually the acids and acid anhydrides having a straight or branched chain hydrocarbon side chain. The hydrophobic agent is used at a level so that the hydrophobic moieties in the final starch products are present at a level of from about 0.1–50% by weight, based upon the total weight of the starch taken as 100% by weight.

In practice, the starch derivatives of the invention exhibit remarkable properties. For example, they exhibit a significant increase in free-flowing characteristics in a dry state. Ordinary starches do not flow freely, but rather tend to agglomerate in clumps or cakes. A second important feature of the starch derivatives is their rapid dispersability or hydration in hot or cold water. The derivatives hereof do not tend to remain in dry mass upon the surface of water, and upon mixing with water the derivatives do not typically rise to the top of the water and form suspensions. Finally, the starch derivatives do not require organic or other wetting agents to facilitate mixing in water and when so mixed to form suspensions are stable under heating without production of paste-like masses. The derivatives of the invention may be used in personal care products such as lotions and sunscreens.

It is believed that the preferred starch derivatives of the invention, being expanded or preswelled and substituted with hydrophobic moieties followed by polyvalent metal substitution have the following generalized structures, in the case of divalent (Formula I) or trivalent (Formula II) metals, wherein R is a di- or trimethylene group, R' is a straight or branched chain hydrocarbon group (especially alkyl, alkenyl or alkynyl groups) having from about 2–20 carbon atoms therein (more preferably from about 6–12 carbon atoms):

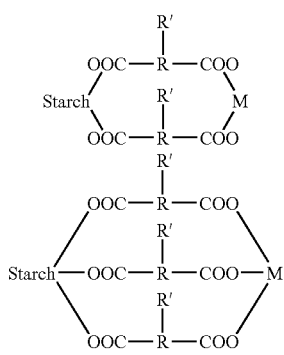

As can be seen, the metal substitution is believed to involve a polyvalent metal ion replacing a hydrogen atom in each of two or more of the hydrophobic moieties to achieve a bridging or cross-linking of such moieties. As will be readily apparent, a bivalent metal ion replaces two hydrogens, a trivalent three, and a tetravalent four.

It is hypothesized that the bridging of hydrophobic moieties results in the formation of a cellular structure in the starch with an apparent decrease in the specific gravity of the starch granules which accounts for the remarkable properties of the derivatives and would be expected to increase the emulsion-forming characteristics of the derivatives as well. Although the products of the invention are referred to as "derivatives", it will be understood that the invention is not limited to any particular structure or nomenclature, i.e., the products could also be characterized as complexes or adducts for example.

It is believed that the swollen and granular morphology of the starch products allows the penetration of water molecules inside the starch granules in aqueous systems. In like manner, in oil and water systems the swollen granular structure of the starch together with the presence of the hydrophobic substituents enable the formation of very stable oil/water/starch emulsions.

DESCRIPTION OF THE PREFERRED EMBODIMENTS

Figure 1:
FIGS. 1 and 2 are a 2000X SEM photograph of a starch (SRS) granules prepared using 2% STMP and 25% OSA, followed by treatment with 5% by weight of aluminum sulfate.
Figure 2:
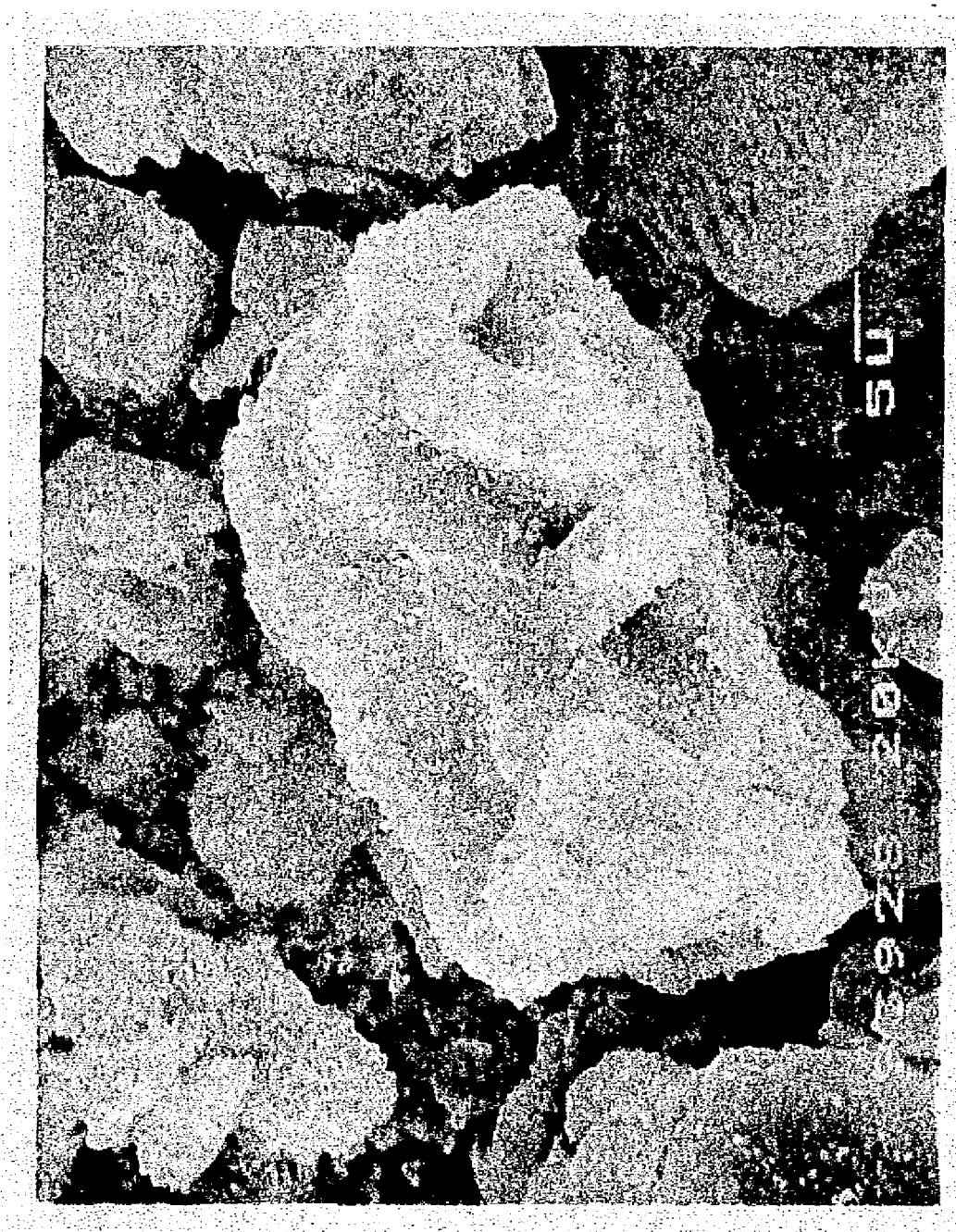
Figure 3:
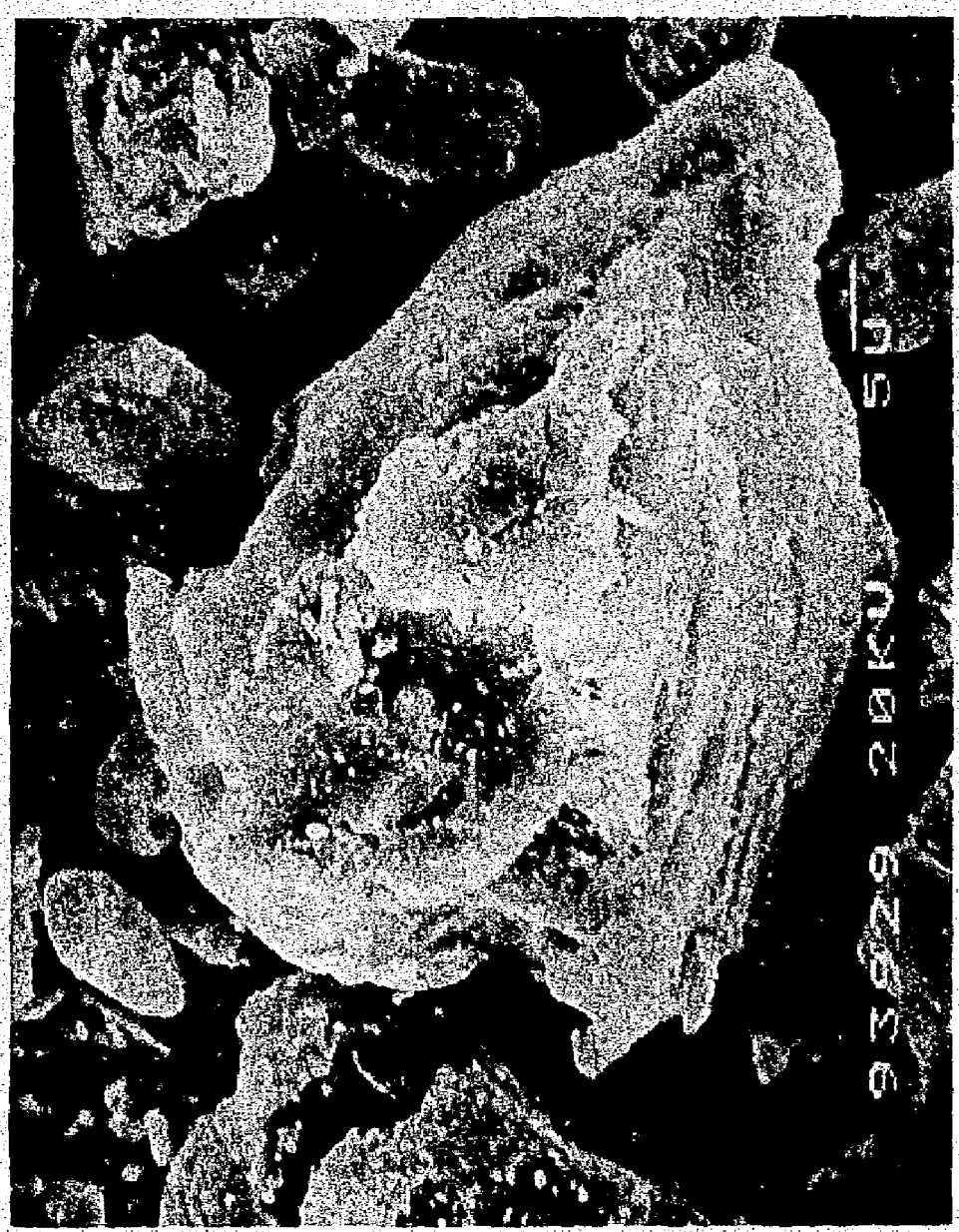
FIGS. 3–4 are respectively 2000X SEM photographs of starch (SRS) granules prepared using 2% STMP and 25% OSA, followed by treatment with 5% by weight of titanium oxide.
Figure 4:
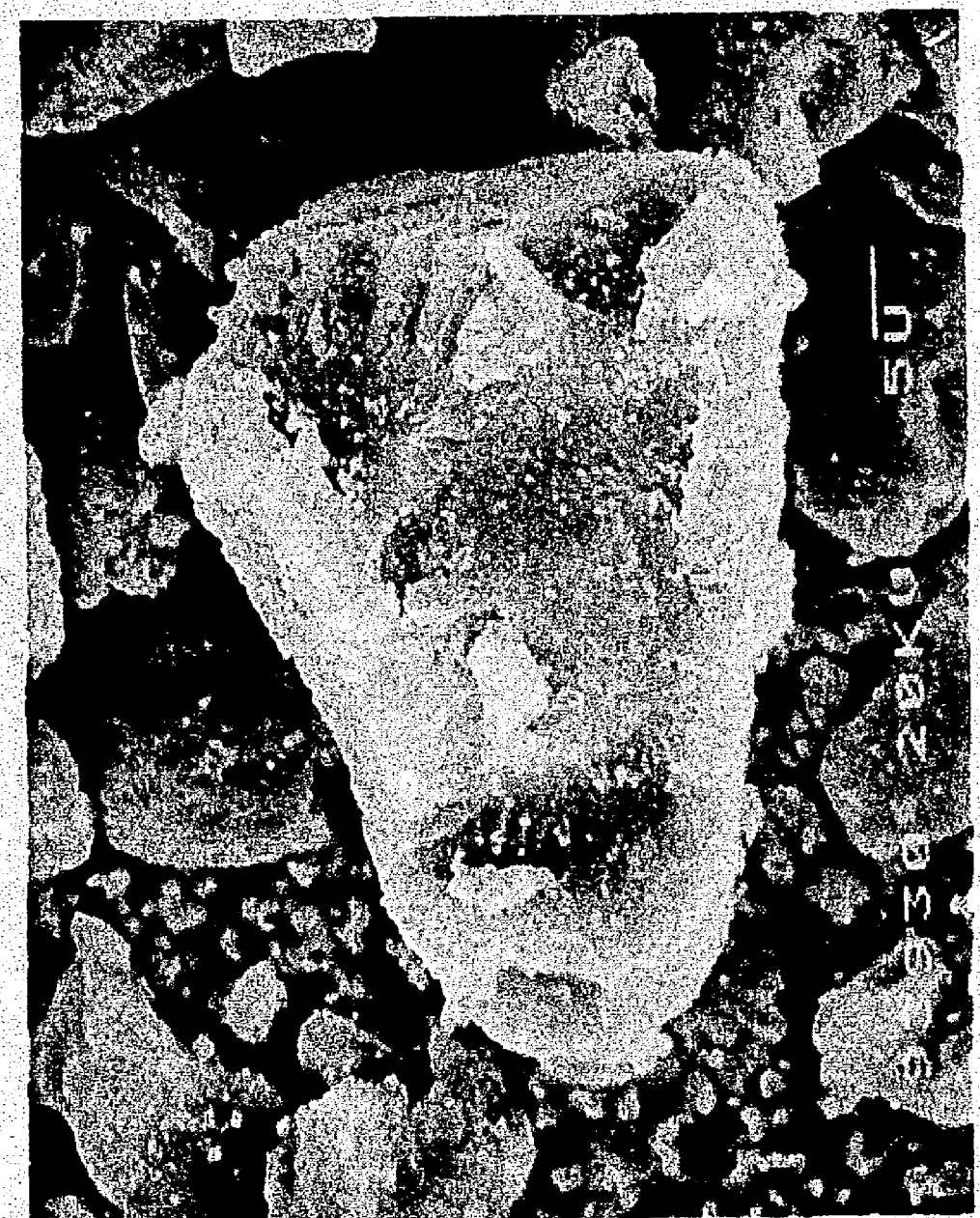

A variety of different starches may be derivatized in accordance with the invention, and indeed essentially any starch can be so modified. Preferable however, the starches are selected from the group consisting of wheat, waxy wheat, corn, waxy corn, high amylose corn, oat, rice, tapioca, mung bean, and potato starches and mixtures thereof.

The starches useful in the invention can be used in their native form by substitution with a polyvalent metal selected from the group consisting of Groups 2–10, inclusive. However, it is preferred that the starches be initially cross-linked and substituted with hydrophobic moieties before reaction with polyvalent metal. Cross-linking may be effected in a number of ways using an assortment of different cross-linking agents, such as those selected from the group consisting of sodium, trimetaphosphate (STMP), sodium tri-polyphosphate (STPP), phosphoryl chloride, epichlorohydrin and mixtures thereof. However, it is particularly preferred that the cross-linking reaction be carried out by preswelling the starch granules in the presences of an alkali (e.g., alkali metal hydroxide) and a salt (e.g., alkali or alkaline earth metal chloride, sulfate or carbonate). The alkali is present to promote swelling of the starch, whereas the salt is added to prevent excess swelling leading to complete destruction of the granular structure of the salt (i.e., gelatinization). Preferred preswelling/cross-linking conditions and parameters are set forth in U.S. Pat. No. 6,299,907 which is expressly incorporated by reference herein.

In more detail, the most preferred initial cross-linking reaction involves a process of first forming a dispersion of starch granules in water where the granules undergo swelling in the dispersion and have a crystalline phase. A cross-linking agent is added to the dispersion while the granules are swelled in order to cross-link the swelled granules, the cross-linking being carried out under conditions to avoid complete gelatinization of the swelled granules. Thereafter, the cross-linked starch granules are heated in excess water in order to melt the crystalline phase of the granules.

In a preferred procedure, the starch granules are preswelled by first forming a starch/water dispersion and heating the latter in order to swell the granules prior to the addition of the cross-linking agent; the preswelling step is preferably carried out in the presence of a base (such as an alkali metal hydroxide which promotes swelling) and a salt (such as an alkali or alkaline earth metal chloride, sulfate or carbonate). Again, it is important that the preswelling and cross-linking steps be carried out so as to avoid complete gelatinization of the starch granules. Accordingly, the temperature of the starch dispersion during preswelling is generally 5–10° C. below the starch gelatinization temperature. It is also possible to preswell the starch at elevated temperatures, for example 70–80° C. if high concentrations (greater than about 20% based on starch) of salt are used with reduced amounts of base. The hydroxide is normally present at a level of about 1–3% by weight based upon starch, while the salt is used at a level of from about 0.1% by weight on the same basis. The pH of the preswelling system is generally from about 10–12.

During the cross-linking step, the dispersion should have from about 20–40% by weight of starch solids therein. The cross-linking step generally involves heating to a temperature of from about 30–75° C. for a period of from about 0.1–12 hrs, more preferably from about 0.5–2 hr. When the preferred STMP cross-linking agent is used the level of use is typically from about 0.1% by weight, on a dry starch basis. During cross-linking, if an inadequate level of STMP is employed, the starch will eventually gelatinize and cause the reaction mixture to gel. When this occurs, swelling has not been counterbalanced by sufficient inhibition from cross-linking. Increasing the temperature of the cross-linking reaction is a compromise between accelerating the swelling and accelerating the cross-linking reaction, such that gelling of the reaction mixture does not occur prior to sufficient cross-linking in a reasonable period of reaction time. After reacting at a warm temperature usually for several hours, the mixture is neutralized and the starch isolated from the salts to give quantitative product yields. The product exhibits an X-ray diffraction pattern very similar to the starting starch, and a gelatinization temperature somewhat elevated as compared with the parent starch.

In the next preferred preparative step, the partially crystalline, swollen/cross-linked starches are heated in excess water followed by drying in order to melt the crystalline phase. For example, a 10% aqueous slurry of the partially crystalline product may be heated to boiling with stirring for about 5 min. to achieve this end. The boiled product is then cooled and centrifuged. The liquid fraction contains at most 1–2% of the original weight of the partially crystalline modified starch in the form of soluble and damaged starch. If the starches are merely tray dried without removal of the soluble and damaged starch fraction, the product may form a cake-like structure comprised of granules that cling together. In lieu of centrifugation, the starch products may be spray dried.

Although preferred, the above-described preswelling/cross-linking procedure is not essential and suitable starches can be prepared using straightforward cross-linking strategies without preswelling. These cross-linking reactions are entirely conventional and need not be described in detail.

The initially cross-linked starches are next preferably subjected to a substitution reaction with a hydrophobic agent so that hydrophobic moieties or residues become chemically bonded or attached to the surfaces of the starch granules. The preferred substitution reaction is carried out in a aqueous solvent or system, normally using an acid or acid anhydride hydrophobe, especially those of the formula

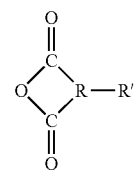

where R is a di- or trimethylene group and R' is a straight or branched chain hydrocarbon group having from about 2–20 carbon atoms therein; preferred agents have from about 6–12 carbon atoms and are selected from the group consisting of straight or branched chain alkyl, alkenyl or alkynl groups. The single most preferred hydrophobic agent is octenyl succinic and hydride (OSA). The hydrophobic agent is used at a level so that the moieties thereof are present in the modified starch at a level of from about 0.1–50% by weight, based upon th total weight of the starch taken as 100% by weight, more preferably from about 1–30%, and most preferably from about 5–25% by weight.

The substitution reaction is usually carried out at pH of from about 7–11, more preferably from about 8–9. The temperature should be from about 10–50° C. and more preferably from about 25–45° C. Reaction times are variable depending upon the degree of substitution desired, but generally range from about 1–12 hours, more preferably from about 2–6 hours. It is normally preferred that the substitution reaction be conducted with continuous agitation. At the end of the reaction, the reaction mixture maybe neutralized with acid to a pH of from about 5–7, more preferably of about pH 6. Thereafter, the starch products maybe water washed and then gelatinized in a hot aqueous system at a temperature of from about 50–150° C., more preferably from about 50–85° C. The final step involves recovery and drying of the modified starch, which is preferably accomplished by spray drying. This step can be done after the metal substitution reaction to facilitate washing. Because fully gelatinized starch takes up more water and takes more water to wash residual salts.

The metal substitution reaction using the expanded or preswelled and hydrophobic moiety-substituted starches is relatively straightforward and generally involves merely contacting the starches with an aqueous dispersion of a selected polyvalent metal salt. This is followed by an appropriate degree of mixing or agitation to achieve the final metal ion substitution. It is not required nor preferred to heat the starch during the final metal substitution reaction, i.e., the reaction is normally carried out at room temperature and pressure.

As indicated above, a wide variety of polyvalent metals may be reacted with the preferred cross-linked starch products. These metals are generally selected from the group consisting of the polyvalent metals of Groups 2–13, inclusive. Any suitable salt of these metals can be employed so long as the salt has sufficient dispersability in aqueous media. Typical salts are the sulphates, chlorides, fluorides, bromides, oxides, carbonates, nitrates and phosphates, although this list is in no way limiting.

The following Examples set forth preferred methods for producing the starch derivatives of the invention. It is to be understood, however, that these Examples are provided by way of illustration only, and nothing therein should be taken as a limitation upon the overall scope of the invention.

EXAMPLE 1

This example describes the production of cold water swellable granular wheat starch cross-linked with STMP, substituted with OSA and complexed with aluminum sulfate.

In the first step, 100 parts (db) wheat starch was dispersed with 233 parts of water and 2 parts of sodium sulfate. The dispersion was warmed to 45° C., whereupon 3 parts of 1M sodium hydroxide solution were slowly added with continued heating and stirring for 1 h. Next, 3 parts of sodium sulfate and 2 parts STMP were added, followed by continued heating and continuous stirring for 16 h. The starch slurry was then adjusted to pH 9.0 with sodium hydroxide and then cooled to room temperature. (25° C.). 5 parts of OSA were next added to the slurry. The slurry was heated for 4 h with continuous mixing and pH maintenance at between 8.0–9.0. The reaction mixture was then neutralized with 1 M HCl, and cooled to 25° C.

5 parts aluminum sulfate were added to the neutralized mixture with mixing for 4 h. The starch was washed 4 times using 4000 parts of water per wash. The recovered starch was then completely gelatinized by heating at 75° C. for 30 min in 4000 parts of water. Final product was recovered by spray drying.

EXAMPLE 2

In this example, modified wheat starch products were prepared as set forth in Example 1, except that OSA level was varied, namely, 1, 2, 10, 25% by weight respectively, as compared with 25% in Example 1.

EXAMPLE 3

In this example, modified wheat starch products were prepared as set forth in Example 1, except that the level of STMP was varied, namely, 0.1, 0.5, 1.0% by weight respectively, as compared with 2% in Example 1.

EXAMPLE 4

In this example, modified wheat starch products were prepared as set forth in Example 1, except that level of aluminum sulfate was varied, namely, 0.1, 1, 2, 10% by weight respectively, as compared with 5% in Example 1.

EXAMPLE 5

In this example, modified wheat starch products were prepared as set forth in Example 1, except that the level of titanium oxide was 5% by weight was used in lieu of aluminum sulfate.

EXAMPLE 6

In this case a modified corn starch product was prepared. 100 parts corn starch were dispersed in 233 parts water with the addition of 10 parts sodium sulfate. The dispersion was warmed to 55° C. and 3 parts of an aqueous 1 M sodium hydroxide solution were slowly added with stirring for 1 hour at temperature. Thereafter, 5 parts sodium sulfate and 2 parts STMP were added with continuous stirring over 16 hours at temperature. The starch slurry was adjusted to pH 9 with sodium hydroxide, and cooled to room temperature (25° C.). 5 parts OSA were then added to the slurry and the pH was maintained between 8.0–9.0 for 4 hours with continuous stirring. The reaction mixture was then neutralized with 1 M HCl, and cooled to 25° C. 5 parts aluminum sulfate were added and mixed for 4 h. The starch was washed 4 times using 4000 parts of water per wash. The recovered starch was then completely gelatinized by heating at 75° C. for 30 min in 4000 parts of water. Final product was recovered by spray drying.

We claim:

1. A starch-polyvalent metal derivative comprising starch granules selected from the group consisting of wheat, waxy wheat, corn, waxy corn, high amylose corn, oat, rice, tapioca, mung bean, and potato starches and mixtures thereof which are prepared by initially expanding starch granules in water, reacting the expanded granules first with a cross-linking agent selected from the group consisting of sodium trimetaphosphate, sodium tripolyphosphate, phosphoryl chloride, eplchiorohydrin and mixtures thereof, and then with an agent to bond or attach hydrophobic moieties to the surface of the granules, said moieties derived from hydrophobic acids and acid anhydrides, and thereafter reacting the reacted granules with a polyvalent metal, selected from the group consisting of Groups 2–13, inclusive, of the Periodic Table, said starch derivative being rapidly dispersible in both hot and cold water.

2. The derivative of claim 1, said metal being selected from the group consisting of the Group 2 metals of the Periodic Table.

3. The derivative of claim 1, said hydrophobic moieties being bridged by said polyvalent metal.

4. The derivative of claim 3, said hydrophobic moieties being present at a level of from about 0.1–50% by weight, based upon the total weight of the starch taken as 100% by weight.

5. The derivative of claim 4, said level-being from about 1–30%.

6. The derivative of claim 5, said level being from about 5–25%.

7. The derivative of claim 1, said moieties derived from acid anhydrides of the formula

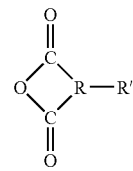

wherein R is a di- or trimethylene group and R' is a straight or branched chain hydrocarbon group having from about 2–20 carbon atoms therein.

8. The derivative of claim 7, wherein R' is a straight or branched chain alkyl, alkenyl or alkynl group.

9. The derivative of claim 7, wherein R' has from about 6–12 carbon atoms therein.

10. The derivative of claim 3, said moieties derived from octenyl succinic anhydride.

11. The derivative of claim 1, said metal selected from the group consisting of the alkaline earth metals, zinc and aluminum.

* * * * *